United States Patent [19]

Taylor

[11] Patent Number: 4,758,518

[45] Date of Patent: Jul. 19, 1988

[54] D-2-HALOALKANOIC ACID HALIDOHYDROLASE

[75] Inventor: Stephen C. Taylor, Darlington, England

[73] Assignee: Imperial Chemical Industries PLC, London, England

[21] Appl. No.: 789,765

[22] Filed: Oct. 21, 1985

[30] Foreign Application Priority Data

Oct. 25, 1984 [GB] United Kingdom ................. 8427032
Dec. 18, 1984 [GB] United Kingdom ................. 8431923

[51] Int. Cl.$^4$ .................. C07B 19/02; C12N 9/14; C12N 1/20; C12R 1/39; C12R 1/40
[52] U.S. Cl. .................................. 435/280; 435/195; 435/253; 435/876; 435/877
[58] Field of Search ............... 435/136, 139, 146, 195, 435/253, 876, 877, 280, 172.1

[56] References Cited

FOREIGN PATENT DOCUMENTS 1473145 11/1967 France.

OTHER PUBLICATIONS

Chem. Abs., 98, 105724r (1983)—abstract of Japanese kokai JP 57, 125691.
Chem. Abs., 97, 180165s—abstract of Japanese kokai JP 82, 125690.
Biotechnology and Bioengineering, 26, 805-806 (1984).
Acta Microbiol., 131, 179-183 (1982).
Hoppe-Seyler's Z. Physiol. Chem., Bd. 364, S 529-535, May 1983.
Agric. Biol. Chem., 46(3), 837-838 (1982).
EP3890A.
J. Gen. Microbiol., 128, 1755-1762 (1982).
European Journal of Biochemistry, 21, 99-109 (1971).

*Primary Examiner*—Lionel M. Shapiro
*Attorney, Agent, or Firm*—Cushman, Darby & Cushman

[57] ABSTRACT

An enzyme composition comprising a D-2-haloalkanoic acid halidohydrolase, bacteria containing said enzyme, a process for the preparation of said enzyme as a cell-free composition and a process in which the enzyme is used to increase the concentration of the L-enantiomer in a mixture of the D- and L-enantiomers of a 2-haloalkanoic acid. Preferably the 2-haloalkanoic acid is 2-bromo- or 2-chloro-propionic acid and the process for increasing the concentration is carried out under anaerobic conditions.

10 Claims, No Drawings

D-2-HALOALKANOIC ACID HALIDOHYDROLASE

This invention relates to enzymes, to bacteria containing such enzymes and to the use of such enzymes in the production of 2-haloalkanoic acids.

2-Haloalkanoic acids, e.g. 2-chloropropionic acid (hereinafter referred to for convenience as 2-CPA), are useful as intermediates in the production of inter alia pyridyloxy-phenoxy substituted alkanoic acids (which acids are hereinafter referred to for convenience as "PPAA's"). Certain PPAA's, e.g. D-2-(4-5(trifluoromethyl-2-pyridyloxy) phenoxy)-propionic acid and lower alkyl esters thereof, are useful as herbicidal compounds, particularly against grass species, as is more fully described in our European Patent Application Publication No. 0003890A.

By "2-haloalkanoic acids" (which are hereinafter referred to for convenience as "2-HAA's") we mean alkanoic acids which bear one fluoro, chloro, bromo, or iodic radical on the carbon atom adjacent the carboxyl group and in which the alkyl group, which may be linear or branched contains two to six carbon atoms. We do not exclude the possibility that the alkyl group may bear a polar substituent which does not react adversely with the enzymes or bacteria as hereinafter defined.

It will be appreciated that the 2-carbon atom in certain 2-HAA's and in the alkanoic acid residue in PPAA's is an asymmetric carbon atom and that, accordingly, the compounds can exist in two enantiomeric forms. One of these forms possesses the D-absolute configuration, i.e. the same absolute configuration as dextrorotatory glyceraldehyde, and the other possesses the L-absolute configuration. These enantiomers are mirror images of each other and are optically active, rotating plane-polarized light in opposite directions.

In European Patent Application Publication No. 0003890A it is disclosed that the D enantiomer of a particular PPAA possesses greater herbicidal activity than the L enantiomer. It is also disclosed in "The Pesticides Manual", 7th Edition, Edited by C. R Worthing, published by the British Crop Protection Council (pages 184 and 345), that the herbicides "DICHLORPROP" and "MECOPROP" are produced as racemates although only the D(+) isomer has herbicidal activity.

It is further disclosed in European Patent Application Publication No. 0003890A that the D-enantiomers of PPAA's can be prepared from the L-enantiomers of the Corresponding 2-HAA.

Preparation of the L-enantiomers of 2-HAA's using classical techniques based on optical isomer separation of a racemic mixture tends to be expensive. We have now devised a biochemical process for such preparation. The process is based on the preferential dehalogenation of the D-enantiomer of a 2-HAA to produce a 2-hydroxy alkanoic acid and separation of the L-enantiomer of the 2-HAA from the 2-hydroxyalkanoic acid. Furthermore, where the 2-hydroxyalkanoic acid is the D-enantiomer of a lactate this is a commercially attractive process for the preparation thereof. The D-lactate may be used to prepare inter alia the L-enantiomer of, for example, 2-CPA by a Walden inversion as is more fully described in our copending British Patent Application No. 8413155.

Enzymes are known which catalyse the conversion of both the D- and L- enantiomers of 2-CPA into lactates, with either inversion or retention of configuration (Weightman et al, Journal of General Microbiology, 1982, Volume 128, pages 1755–1762). Enzymes are known which catalyse the conversion of only the L-enantiomer of 2-CPA into lactate with inversion (Little et al, European Journal of Biochemistry, 1971, Volume 21, pages 99–109). Enzymes which convert only the D-enantiomer of 2-CPA into lactate have not previously been known. We have now discovered an enzyme which is capable of catalysing the conversion of the D-enantiomers of 2-HAA's, or suitable derivatives thereof, into 2-hydroxy compounds but is not capable of catalysing the conversion of the L-enantiomers of 2-HAA's, or suitable derivatives thereof into 2-hydroxy compounds.

Enzymes which are capable of catalysing the conversion of the D-enantiomers of 2-HAA's, or suitable derivatives thereof, into 2-hydroxy alkanoic acids or suitable derivatives thereof and are incapable of catalysing the release of halogen residues from the L-enantiomers of 2-HAA's, or derivatives thereof, are hereinafter referred to for convenience as "D-2-HHA-halidohydrolases".

According to a first aspect of the present invention there is provided a cell-free enzyme composition which comprises a D-2-HAA-halidohydrolase which is produced by a bacterium, which cell-free enzyme composition is substantially free of any enzyme activity which is capable of metabolising a L-2-HAA or derivative thereof.

According to a second aspect of the present invention there is provided a bacterium which comprises a D-2-HAA-halidohydrolase and which does not contain an enzyme which is capable of metabolising a L-2-HAA or derivative thereof.

According to a third aspect of the present invention there is provided a process for increasing the concentration of the L-enantiomer in a mixture of the D- and L-enantiomers of a 2-HAA which process comprises the step of treating the mixture with a D-2-HAA halidohydrolase under conditions such that at least a portion of the D-enantiomer is converted into a 2-hydroxyalkanoic acid or derivative thereof.

According to a fourth aspect of the present invention there is provided a process for the preparation of a cell-free enzyme composition according to the first aspect of the present invention which process comprises culturing a suitable bacterium, lysing the cells, separating the soluble protein fraction therefrom and isolating the desired enzyme composition.

According to a fifth aspect of the present invention there is provided a process for increasing the concentration of the L-enantiomer in a mixture of the D- and L-enantiomers of a 2-HAA which process comprises the step of treating the mixture with a D-2-HAA halidohydrolase under conditions such that at least a portion of the D-enantiomer is converted into a 2- hydroxyalkanoic acid wherein this step is carried out under anaerobic conditions.

The 2-HAA used in the present invention is preferably a 2-bromo or 2-chloro-propionic acid. Whilst we do not exclude the possibility that the carboxyl group may be in the form of a suitable derivative as is more fully described in our European Patent Specification No. 0003890, the carboxyl group is preferably free or in the form of a metal salt thereof, which metal ion does not react adversely with the cell or enzyme. Preferably the metal ion is derived from a metal in Group IA of the Periodic Table of Elements and more preferably is sodium or potassium.

The bacterium of the invention may belong to any genus but is suitably a strain of *Pseudomonas*, especially a strain of the species *Pseudomonas putida* or *Pseudomonas fluorescens*.

5 strains of bacteria which can be used as sources from which the bacteria according to the second aspect of the invention may be derived by mutation or by genetic manipulation and from which the enzyme composition of the first aspect of the invention may be isolated have been deposited at the National Collection of Industrial Bacteria, PO Box 31, 135 Abbey Road, Aberdeen, Scotland, UK, and have been assigned the following accession numbers:

1. *Pseudomonas putida* NCIB 12018
2. *Pseudomonas fluorescens* NCIB 12159
3. NCIB 12160
4. NCIB 12161
5. *Pseudomonas putida* NCIB 12158

These strains and strains derived from them which can be sources of the bacteria of the invention also form a part of the invention.

The processes of the third and fifth aspects of the invention when used to produce 2-hydroxyalkanoic acids together with or in place of the L-enantiomers of 2-HAA's are also included in the scope of the invention particularly when the 2-hydroxyalkanoic acid is lactic acid.

D-2-HAA-Halidohydrolases as hereinbefore defined may be isolated from bacteria, for example *P. putida* NCIB 12018, by techniques well known in the enzyme art, e.g. absorption, elution, and precipitation techniques. For example, cells of a suitable organism may be ruptured, for example in a French pressure cell. The homogenate suspension may be separated into a solid phase and a liquid phase by conventional biochemical separation methods, e.g. centrifugation or filtration, and a cell-free extract in a suitable buffer may be obtained. Suitable buffers include inter alia phosphate, trishydroxymethyl-aminomethane ("Tris"), bicarbonate, glycine, imidazole, etc. The concentration of the buffer solution is typically between 1 mM and 200 mM, e.g. about 25 mM.

The cell-free extract may be fractionated using fractionating techniques which are capable of separating molecules according to inter alia their molecular size and/or charge, for example, ultrafiltration, electrophoresis, e.g. on a polyacrylamide gel, or chromatography, e.g. on a DEAE-Sephacel column. Identification of the appropriate fraction and the isolation therefrom of the enzyme having the desired enzymatic activity may be carried out using techniques known in the art, for example those described by Weightman et al, Journal of General Microbiology, 1980, Volume 121, pages 187-193.

Enzymes according to the first aspect of the present invention have pH optima for dehalogenation activity towards D-2-CPA of 8.5-9.5. They have good activity in organic and in inorganic buffers and they also work in an unbuffered system under appropriate pH control.

The novel bacteria were isolated from soil in the neighbourhood of chemical plants in which 2-CPA was used and were bred to pure forms of superior efficacy with respect to dehalogenation of 2-HAA's or derivatives thereof by strain selection techniques. This involved the utilisation of standard techniques in growing daughter generations and selecting single cell colonies which were then grown in known fermentation media.

We have found that the five strains deposited at NCIB and listed above as sources of the bacteria of the second aspect of the invention contain a second enzyme, which second enzyme is capable of catalysing the conversion of L-2-HAA's, or suitable derivatives thereof, into the corresponding 2-hydroxy compounds.

The process according to the third and fifth aspects of the present invention may be carried out using an intra- or extra- cellular D-2-HAA-halidohydrolase. Where an extra-cellular D-2-HAA-halidohydrolase is used it may be in an "immobilised" or "insolubilised" form. Where an intracellular D-2-HAA-halidohydrolase is used the cells may be in an "immobilised" or "insolubilised" form.

Techniques are known in the art to "immobilise" or "insolubilise" enzymes and cells by suitable known treatment, e.g. flocculation, or by physically or chemically coupling them to essentially insoluble, inert carrier materials, thus facilitating their use in flow through reactors. As used herein the terms "immobilised enzyme" and "immobilised cell" mean an enzyme or cell which is physically or chemically bonded to or entrapped in an insoluble carrier material or has been treated to form an insoluble mass, e.g. flocculated. When the immobilised enzyme is contacted with a liquid in which it is normally soluble, the enzyme remains attached to the carrier material. Where immobilised cells are contacted with a liquid in which the cells are normally readily dispersible the cells remain attached to the carrier material or as a flocculated mass.

Various materials may be used for the carrier. For example, enzymes and cells may be bonded to various organic materials, e.g. various cellulose derivatives, polyaminostyrene beds, etc., or to various inorganic materials, e.g. porous glass and silica gels. Methods for absorbing enzymes to silicous materials are described in U.S. Pat. No. 3,556,945. Inorganic materials, more preferably alkali-resistant ceramics, are preferred.

Techniques for entrapping enzymes and cells in suitable insoluble carrier materials such as gels, e.g. polyacrylamide or carrageenan, or for flocculating them are well known in the art (Burke, Philosophical Transactions of the Royal Society of London, 1983, Volume 300, pages 369-389; Mosbach, Structure and Order in Polymers Lecture International Symposium 1980, Pergammon 1981, pages 231-238).

Where immobilised enzymes or cells are used, they may be used in a continuous type reactor, more preferably a flow through reactor.

Where intra-cellular enzymes are used in the process according to the third and fifth aspects of the present invention, suitable cells may be prepared by, for example, mutation or genetic engineering. For example, cells of a naturally occurring micro-organism which contain a D-2-HAA halidohydrolase and an enzyme capable of catalysing the conversion of a L-2-HAA, or derivative thereof, into the corresponding 2-hydroxy compound may be subjected to a mutation treatment such that the cells lose their ability to react adversely with the L-enantiomer. The mutation treatment may comprise a physical treatment, e.g. exposure to suitable electro magnetic radiation such as UV light, or a chemical treatment with a suitable chemical e.g. N-methyl-N¹-nitro-N-nitrosoguanidine. Suitable chemical treatments include those described by Ornston (Journal of Biological Chemistry, 1966, Volume 241, pages 3800-3810).

Alternatively, genetic information which codes for a D-2-HAA-halidohydrolase may be transferred from a microorganism in which it occurs naturally to a suitable foreign organism, i.e. an organism in which it does not naturally occur. For example, the plasmid, on which the genes coding for D-2-HAA-halidohydrolase may be carried (Kawasaki et al, Agricultural and Biological Chemistry, 1981, Vol., 45, pages 29–34) may be isolated by known techniques, e.g. a salt precipitation technique (Guerry et al, Journal of Bacteriology, 1973, Volume 116, pages 1064–1066), and may be further purified by known techniques, e.g. by cesium chloride-ethidium bromide density gradient centrifugation. The gene may be introduced into the foreign organism by known methods, e.g. transformation. Alternatively, the gene may be transferred directly to a second organism by, for example, cell conjugation, which process may require mobilisation (Beaching et al, J. Gen. Microbiol., 1983, Vol. 129, pages 2071 to 2078).

As examples of suitable foreign organisms which, it will be appreciated, do not adversely affect production of the D-2-HAA-halidohydrolase nor react adversely with the L-enantiomer of 2-HAA's, may be mentioned inter alia. *Escherichia coli, Methylophilus methylotrophus* (particularly the strains NCIB Nos. 10508 to 10515 and 10592 to 10596 which are described in our UK Patent Specification No. 1370892) and *Bacillus subtilis.*

Where the process according to the third and fifth aspects of the present invention is carried out in the presence of an intra-cellular D-2-HAA-halidohydrolase cells of a suitable organism may be grown in a conventional growth medium by a continuous, batch or fedbatch technique. The growth medium typically comprises an aqueous mineral salts solution and a suitable carbon source e.g. glucose, ethanol, acetic acid or 2-HAA. The concentration of the carbon source can vary over a wide range but is generally between 1% ($^w$/v) and 5% ($^w$/v). Oxygen or an oxygen containing gas, must be present during the growth period. The temperature of the medium during the growth period may vary considerably but normally will be in the range of 25° C. to 35° C. The pH of the medium is kept within the range of 5.5 to 8.0 during growth and preferably at 6.5 to 7.5. The size of the culture can vary considerably for example between 1.5 and 50,000 liters.

Following the growth period the cells are used in the process of the third and fifth aspects of the present invention. The cells may be harvested, for example by centrifugation or flocculation, or they may be used directly in the aforesaid process. Where the cells are harvested they are resuspended in a buffer solution which does not support significant cell growth, e.g. phosphate, bicarbonate or tris (hydroxymethyl) aminomethane buffer solutions or water. Typically the concentration of resuspended cells is 1 to 30 grams dry weight per liter. The cells are kept at a temperature between 20° C. and 40° C. and the pH maintained between 5.5 and 9.5.

The culture is then contacted with the mixture of 2-HAA or a suitable derivative thereof, for example a lower alkyl ester or, preferably a salt, e.g. a sodium or potassium salt, thereof by methods well known in the art. The productive lifetime of the cell suspension is typically between 5 and 1000 hours. After this period the cells are removed by centrifugation and/or flocculation and/or filtration. Fresh cells may be added to the supernatant liquor and the process repeated. At the end of the process the 2-HAA is preferably extracted from the acidified aqueous reaction mixture by solvent extraction with a suitable polar solvent. Examples of polar solvents which may be used include inter alia diethyl ether, methylene chloride and methylisobutyl ketone. More preferably continuous extraction procedures are employed. However, we do not exclude the possibility that, for example, the aqueous medium, after separation of the cells, (1) is evaporated and the residue dissolved in a suitable solvent, e.g. chloroform or methylene chloride; or (2) is treated with a suitable absorbent, for example by passage down an ion-exchange column; or (3) is treated with a reagent such that the desired compound is precipitated as a salt thereof, e.g. a calcium salt.

The process according to the fifth aspect of the present invention is carried out in a substantially oxygenfree atmosphere since we have found that under reduced oxygen tension the half-life of the enzyme is increased. Preferably the process of this fifth aspect is carried out in a nitrogen atmosphere.

Cells for use in the third and fifth aspects of the present invention may be permeabilised to facilitate movement of substrate and product in and out of the cell. A suitable permeabilisation treatment is described by Felix in Analytical Biochemistry, 1982, Volume 120, pages 211–234.

The L-enantiomer of 2-HAA produced in the process of the third and fifth aspects of the present invention preferably has an optical purity of at least 80%, particularly at least 95% and especially at least 99%.

The present invention is illustrated by reference to the following examples in which the following media were used:

Citrate Buffer 0.1 M citric acid (14.9 mls) and 0.1 M trisodium citrate (35.1 mls) were made up to 500 mls with distilled water. The resulting buffer had a pH of 5.5.

Bauschop and Elsdons Medium (a) Salt solution

Magnesium Oxide (10.75 grams), zinc sulphate heptahydrate (1.44 grams), cobalt sulphate heptahydrate (0.28 grams), calcium carbonate (2.0 grams), manganese sulphate tetrahydrate (1.12 grams), boric acid (0.06 grams), ferrous sulphate heptahydrate (4.5 grams), copper sulphate pentahydrate (0.25 grams), and concentrated hydrochloric acid (51.3 mls) were dissolved separately in water, except magnesium oxide and calcium carbonate which were dissolved separately in a small volume of the concentrated hydrochloric acid. The solutions were mixed and made up to one liter in distilled water.

(b) Stock solution A

Potassium dihydrogen phosphate (500 grams), sodium hydroxide (110 grams) and nitrilo-triacetic acid (50 grams) were dissolved in distilled water and made up to two liters.

(c) Stock Solution B

Ammonium sulphate (200 grams), magnesium sulphate heptahydrate (20 grams), ferrous sulphate heptahydrate (1 gram) and a portion (200 mls) of the Salt Solution were made up to two liters with distilled water.

(d) B-E Minimal Medium

A portion (10 mls) of Stock Solution A, a portion (10 mls) of Stock Solution B and distilled water (48) mls) were mixed to pH 7.0–7.2.

(e) B-E Agar Medium

Difco Bacto agar was added to B-E minimal medium to give a concentration of 2.0% $^w$/v at which concentration a solidified medium was obtained.

Medium A

Medium A was an aqueous solution of ammonium sulphate (5 grams/liter), $MgSO_4.7H_2O$ (0.8 grams/liter), potassium sulpate (0.45 grams/liter), concentrated phosphoric acid (1.3 ml/liter), $FeSO_4.5H_2O$ (0.04 grams/liter) and a trace element solution (60 ml/liter).

The trace element solution contained copper (5 ppm), Mn (25 ppm), Zn (23 ppm) and calcium (720 ppm).

Medium B

Medium B was an aqueous solution of ammonium sulphate (1.8 g $1^{-1}$), magnesium sulphate ($MgSO_4.7H_2O$) (0.2 g $1^{-1}$), ferric chloride (0.97 mg $1^{-1}$), potassium hydrogen phosphate ($K_2HPO_4$) (1.9 g $1^{-1}$), sodium dihydrogen phosphate ($NaH_2PO_4$) (1.56 g $1^{-1}$) and a trace element solution (1 ml $1^{-1}$) as used in medium A.

EXAMPLE 1

This example illustrates the preparation of an enzyme according to the first aspect of the present invention.

1. Isolation of micro-organisms which are capable of degrading 2-CPA.

Samples (1 gram) of soil from locations where HAA's occur naturally, e.g. coniferous forests, and locations where synthetic HAA's are deposited were incubated in B-E minimal salts medium (100 mls) containing the sodium or potassium salt of DL-2-CPA at a concentration of 20 mM for 3 days at 30° C. The culture was then serially diluted onto a sample of the above defined medium which had been solidified with 1.5% $^w$/v agar and incubated at 30° C. for a further 3-7 days. Colonies of bacteria capable of degrading 2-CPA (one of which was *P. putida* NCIB 12018) were picked off for further purification.

2. Detection of an enzyme capable of dehalogenating the D-enantiomer but not the L-enantiomer of 2-CPA.

Samples of the discrete colonies isolated in Step 1 were separately grown in B-E minimal medium (2 liters) at 30° C. with the pH of the medium controlled at 7.0±0.1 by the addition of 2 M potassium hydroxide. The culture was stirred at 1000 rpm while air was added at 0.5 liters/minute. The potassium salt of DL-2-CPA was added to the fermenter at 3 moles per hour.

After 16 hours, the culture was harvested by centrifugation at 5000 G for 20 minutes, the cells were washed with 25 mM phosphate buffer ($NaH_2HPO_4$), pH 7 at 4° C. and then resuspended in 10 mls of the same buffer. They were disrupted by two passes through a French pressure cell at 12000 psi and unbroken cells and cell debris were removed by centrifugation for 1 hour at 120,000 G. A cell-free extract was obtained.

Samples of the cell-free extracts were submitted in duplicate to polyacrylamide gel electrophoresis (Hardman et al, Journal of General Microbiology, 1981, Volume 123, pages 117-128). One of each pair of gels, after electrophoresis was incubated in a buffer solution containing 50 mM D-2-CPA and the other of each pair was incubated in a buffer solution containing 50 mM L-2-CPA as described in the aforesaid Hardman et al reference.

This technique revealed that two halidohydrolases were present in *P. putida* NCIB 12018. One enzyme has activity on L-2-CPA but not on D-2-CPA and the second enzyme has activity on D-2-CPA but not on L-2-CPA, i.e. it is an enzyme according to the first aspect of the present invention.

(D-2-CPA and L-2-CPA may be prepared as described by Fu et al, Journal of the American Chemical Society, 1954, Volume 76, pages 6054-6058).

3. Isolation of dehalogenases

A portion (25 ml) of the cell free extract from *Pseudomonas putida* NCIB 12018 was loaded onto DEAE-Sephacel column (45 mm diameter, 60 cm high) pre-equilibrated with 25 mM Tris/Sulphate buffer at pH 7.5. The column was eluted with portions (200 ml) of this buffer neat and then containing successively 0.15 M, 0.2 M and 0.5 M potassium chloride at a flow rate of 100 ml/hour.

Each of the four fractions was assayed for halidohydrolase activity as described in Step 2 using L-2-CPA and D-2-CPA as substrates.

Activity towards D-2-CPA was found exclusively in the 0.15 M fraction. Activity towards L-2-CPA was found exclusively in the 0.5 M fraction. No halidohydrolase activity was found in the neat buffer fraction nor in the 0.2 M fraction.

4. Properties of D-2-HAA halidohydrolase

The halidohydrolase in the 0.15 M fraction has a pH optimum for activity on D-2-CPA at 8.8-9.0. It has good activity in organic (Tris/Sulphate) and inorganic (bicarbonate/carbonate) buffers, and has activity in unbuffered media, e.g. distilled water, with the pH controlled at 8.8-9.0.

On storage at 4° C. in 0.1 M Tris/Sulphate, pH 9 buffer, the enzyme has a half-life of approximately 10 days.

The enzymatic activity is not inhibited by up to 1 M DL-2-CPA or by the products of the reaction, i.e. chloride ion and lactate, at up to 1 M concentration.

EXAMPLE 2

This example illustrates the use of a D-2-HAA halidohydrolase.

The potassium salt of DL-2-CPA was added to a mixture of a portion (150 ml) of the 0.15 M eluate fraction obtained in Step 3 of Example 1, containing D-2-HAA halidohydrolase from *P. putida* NCIB 12018, and 0.05 M bicarbonate buffer ($NaHCO_3/Na_2CO_3$) at 30° C. with stirring and the pH was maintained at 9.0 by the addition of 2 M aqueous potassium hydroxide. The reaction was followed by monitoring the release of chloride ion. When release of chloride ion stopped additional amounts of DL-2-CPA were added. After 5 hours the concentration of chloride ion was 87 mM and 16 grams (150 moles) of DL-2-CPA had been added.

The reaction mixture was acidified to pH 4 and precipitated protein was removed by centrifugation at 10,000 G for 30 minutes. The clear supernatant liquor was further acidified to pH 2.0 and continuously extracted with methylene chloride. Evaporation of the methylene chloride left 7.3 grams of crude 2-CPA which on distillation gave a main fraction of 5.06 grams of a colourless oil. The oil had 30.4 (-) 12.5o (C = 1.77, CC14) an optical rotation of $[\alpha]_D^{30.4}(-)$ 12.5° (C=1.77, $CCl_4$) corresponding to 2-CPA with a 92:8 L:D ratio (i.e. 84% enantiomeric excess); the identity of the product was confirmed by IR and NMR spectroscopy.

EXAMPLE 3

This example illustrates the preparation of a mutant strain which is incapable of dehalogenating L-2-CPA.

Pseudomonas putida NCIB 12018 was grown overnight in Luria liquid medium at 30° C. in a shaking water bath. It was sub-cultured into fresh Luria liquid medium and grown under the above conditions to an optical density, measured at 550 nanometers, (hereinafter referred to for convenience as "OD-550") of 0.5.

Duplicate samples (15 mls) of the culture were centrifuged and the cell pellets resuspended separately in a solution of N-methyl-N'-nitrosoguanidine (0.75 mgs) in 10 mM citrate buffer (15 mls). The mixtures were incubated on a reciprocating shaker at 30° C. for 45 minutes.

The cells were harvested by centrifugation, and washed twice by resuspension in B-E minimal medium and centrifugation. The pellets were suspended in B-E minimal medium (5 ml) and aliquots (1 ml) were inocculated into B-E minimal medium (2 mls) and 0.3% sodium pyruvate in shaker flasks and incubated at 30° C. until well grown.

After growth, the OD-550 of the cultures was measured, they were diluted, to give approximately 1000 cells per ml, aliquots (0.1 ml) were spread on plates comprising B-E agar medium and sodium pyruvate (10 millimoles) and incubated at 30° C. until colonies appeared. Samples of the colonies were replica plated onto B-E medium plates containing 10 mM D-2-CPA and 10 mM L-2-CPA. Replica pairs of plates were compared and colonies were isolated which grew on D-2-CPA but not on L-2-CPA. They were compared for growth on L- and D-2-CPA and pyruvate and those with the desired phenotype and which showed little reversion were selected for further testing (Table 1)

TABLE 1

| Run Number | 1 | 2 | 3 | 4 |
|---|---|---|---|---|
| Colonies Screened | $6.4 \times 10^3$ | $6.6 \times 10^3$ | $5.6 \times 10^3$ | $6.9 \times 10^3$ |
| $L^-D^+$ 2-CPA colonies isolated | 39 | 7 | 117 | 173 |
| Isolates retained for testing | 5 | 1 | 2 | 0 |

Samples of the isolates were grown overnight in B-E minimal medium (20 ml) containing DL-2-CPA (20 mM) at 30° C. with shaking. Cultuires were centrifuged at 10,000 G for 20 minutes and the cells were resuspended in Tris/Sulphate buffer, 0.1 M, pH 8.8 (10 ml). Each cell suspension was divided into two 5 ml aliquots.

One aliquot from each pair was made up to 40 mM with D-2-CPA and the other was made up to 40 mM with L-2-CPA. Each aliquot was then incubated with shaking at 30° C. for 24 hours and the release of chloride ion was followed.

One mutant (hereinafter referred to for convenience as AJ1-23) released chloride ion from D-2-CPA at a rate of 8.5 millimoles chloride per hour per gram of cell dry weight but did not release chloride from L-2-CPA.

EXAMPLE 4

This example illustrates the use of a mutant strain which is capable of releasing chloride ion from D-2-CPA but not from L-2-CPA.

A sample of the mutant strain, AJ1-23 prepared in Example 3 was grown on B-E liquid medium containing 0.3% $^w/v$ sodium pyruvate as carbon source as a chemostat culture (500 ml) at a dilution rate of 0.1 per hour, temperature 30° C., and aeration 1 volume/volume/minute. 5 liters of spent culture from the chemostat waste pot were harvested by centrifugation.

The cells were resuspended in 0.1 M sodium bicarbonate/carbonate buffer (180 ml), pH 9, containing 200 millimoles of the potassium salt of racemic 2-CPA. The reaction mixture was stirred at 500 rpm at 30° C. and the pH was maintained at 8.8 by addition of 4 M aqueous potassium hydroxide. After 22 hours, additional cells from the waste pot were added and the reaction continued for a further 20 hours. The cells were then removed by centrifugation. The supernatant solution was acidified to pH 4 with concentrated sulphuric acid and the resulting precipitate was removed by centrifugation. The clear solution was extracted with methylene chloride, the L-enantiomer of 2-CPA (3.5 grams) was isolated and was found to have an optical purity of 82% (64% enantiomeric excess).

EXAMPLE 5

This example illustrates the use of a mutant strain according to the fifth aspect of the invention, to produce L-2-CPA of high enantiomeric purity.

A sample of the mutant strain AJ1-23 prepared in Example 3 was grown as a chemostat culture as described in Example 4.

A portion (400 ml) of the culture was used to inoculate Medium A (6 lites) and glucose was added continuously to the mixture at a rate of 0.75 grams/liter/hour. The mixture was stirred at 500 rpm, air was added at 4 liters/minute, the pH was maintained at 7.0, by the addition of 2 M NaOH, and the temperature was maintained at 30° C. After 24 hours, the cell density was approximately 8 grams cell dry weight/liter, and addition of glucose was stopped. DL-2-CPA was then added at a rate of 20 mmoles per hour for 20 hours. The cells were harvested by centrifugation.

A portion (8 grams dry weight) of the harvested cells were resuspended in 50 mM potassium phosphate buffer (900 ml), at pH 7.4, containing the sodium salt of DL-2-CPA (108 grams). The mixture was stirred at 250 rpm, its temperature was maintained at 30° C., nitrogen was passed over the top of the mixture to maintain an essentially oxygen-free blanket above the mixture and 4 M sodium hydroxide solution was added as required to maintain the pH at 7.4±0.2.

After 20 hours reaction, there was no further release of chloride ion, the reaction mixture was divided into two portions (Portion A and B). Portion A was acidified to pH 1 with sulphuric acid, filtered through diatomaceous earth, continuously extracted with methylene chloride, and the methylene chloride extract was evaporated to dryness to leave an oil (25.52 grams). Short path distillation yielded a fraction (19.0 grams) which, as a 0.87% solution in carbon tetrachloride, had an $[\alpha]_D^{30}$ of $-13.3°$. This fraction was shown by nmr to be L-2-CPA containing less than 2% of D-2-CPA (i.e. 96% enantiomeric excess).

EXAMPLE 6

This example illustrates the release of chloride ions from D-2-CPA, in the presence of a bacterium according to the third aspect of the present invention immobilised on a suitable support.

A mixture of AJ1-23 (0.4 grams dry weight), grown in a chemostat as described in Example 4, a 30% $^w/v$ aqueous acrylamide solution (6.1 ml), a 2% $^w/v$ aqueous bis-acrylamide solution (1.25 ml) and 1 M Tris-sulphate buffer, pH 8.7 (10.75 ml) was degassed under vacumm and then N,N,N¹,N¹-tetramethyl-ethylenediamine (37 microliters) and 10% w/v ammonium persulphate (60 microliters) were added to initiate polymerisation. After 30 minutes, the resultant solid gel containing immobilised cells was forced through the orifice of a 10 ml syringe and then washed with 1 M, pH 8.7 Tris/sulphate buffer.

The aforementioned immobilised cells were incubated, with gentle shaking, at 30° C. in o.5 M pH 8 phosphate buffer (10 ml) containing the sodium salt of DL-2-CPA (5 mmoles). The activity of the cells was measured by following the release of chloride ion. Release of chloride continued for at least 200 hours at which time the chloride ion concentration was 130 mM.

EXAMPLE 7

Isolation of additional microorganism from the environment which contain D-2-HAA-halidohydrolases.

Samples of soil (2 g), collected from sites in the UK where chlorinated acids are polutants, were incubated with shaking at 30° C. in 100 ml volumes of mineral salts medium (medium B) containing 20 mM DL-2-CPA, sodium salt, as sole carbon source. After 3 days, aliquots of each enrichment culture thus produced were plated after serial dilution on the above medium solidified with agar. Colonies of microorganisms which appeared after 2–5 days were isolated and bred to pure form by standard microbiological techniques.

Samples of each organism were grown for 16 hours in 200 ml amounts of the same medium after which time the cells were harvested by centrifugation and resuspended in 20 mM Tris-sulphate buffer, pH 7.8 to give an approximate cell density of 50 g dry weight $1^{-1}$. The rate of dechlorination by each organism of both L-2-CPA, Na+ salt, and DL-2-CPA, Na+salt, was measured as described in Example 2. Those organisms which showed a higher rate of dechlorination of DL-2-CPA than L-2-CPA were further studied, (Table 2).

Cell-free extracts of those organisms were prepared as described in Example 1 and their dehalogenase complement was examined as described previously by electrophoresis. Gels were examined for activity with L-2-CPA and D-2-CPA and the substrate specificity of each dehalogenase protein was noted, (Table 3). Dehalogenases specific to D-2-CPA and showing no activity on L-2-CPA were found.

TABLE 2

Rates of dechlorination of L- and DL-2-CPA by microbial isolates.

| microorganism | Rate (mmoles cl⁻ released $h^{-1}$g dry weight of cells) | |
|---|---|---|
| | DL-2-CPA | L-2-CPA |
| 1. *Pseudomonas putida* NCIB 12158 | 67.8 | 31.6 |
| 2. *Pseudomonas fluorescens* NCIB 12159 | 35.4 | 13.9 |
| 3. NCIB 12160 | 28.8 | 9.1 |
| 4. NCIB 12161 | 65.3 | 16.6 |

TABLE 3

Substrate specificities of individual dehalogenases of microbial isolates as determined by electrophoresis.

| Microorganism | Dehalogenase specificities | |
|---|---|---|
| | Enzyme 1 | Enzyme 2 |
| *P. putida* NCIB 12018 | D-2-CPA | L-2-CPA |
| *P. putida* NCIB 12158 | D-2-CPA | L-2-CPA |
| *P. fluorescens* NCIB 12159 | D-2-CPA | L-2-CPA |
| NCIB 12160 | D-2-CPA | DL-2-CPA |
| NCIB 12161 | D-2-CPA | DL-2-CPA |

EXAMPLE 8

Use of the D-2-HAA-halidohydrolases from *P. putida* NCIB 12018 and mutant AJ1-23 to debrominate selectively D-2-bromopropionic acid (D-2-BPA) as a racemic mixture.

100 μl cliquots of an enzyme preparation produced as described in Example 1 were incubated for 16 h with various concentrations of DL-2-BPA, Na+ salt, in 30° C. ° in 0.5 M potassium phosphate buffer at pH 7.3. (Final volume 5 ml).

Mutant AJ1-23 produced as in Example 3 was similarly treated (final cell concentration 1 g dry weight $1^{-1}$). After 16 h the quantity of bromide ion in the reaction mixture was measured with a Marious Chloro-O-Counter as, described above. In each case 50% of the DL-2-BPA had been debrominated, indicating isomer selectivity (Table 4).

TABLE 4

| | Initial conc. of DL-2-BPA | Conc. of Br⁻ released |
|---|---|---|
| isolated enzyme from NCIB 12018 | 0.5 M | 0.26 M |
| | 0.2 M | 0.10 M |
| | 0.1 M | 0.05 M |
| | 0.05 M | 0.03 M |
| AJ1-23 | 0.2 M | 0.11 M |

EXAMPLE 9

Use of D-2-CPA contained within mutant organism AJ1-23, to produce L-2-CPA high enantiomer excess on a semi-technical scale.

Mutant AJ1-23 was grown in 2×600 ml cultures of the mineral salts medium used in Example 4 containing 0.3% w/v sodium pyruvate and 10 mM DL-2-CPA at 30° C. After 24 hours cultures were incubated into 500 l of a medium containing the following ingredients:

| | |
|---|---|
| $MgSO_4.7H_2O$ | 1.01 g $1^{01}$ |
| $(NH_4)_2SO_4$ | 6.3 g $1^{-1}$ |
| $K_2SO_4$ | 0.57 g $1^{-1}$ |
| $FeSO_4.7H_2O$ | 0.05 g $1^{-1}$ |
| $MnSO_4.7H_2O$ | 0.0078 g $1^{-1}$ |
| $ZnSO_4.7H_2O$ | 0.0078 g $1^{-1}$ |
| $CuSO_4.5H_2O$ | 0.0015 g $1^{-1}$ |
| $CaCl_2$ | 0.15 g $1^{-1}$ |
| $H_2SO_4$ (conc) | 0.15 ml $1^{-1}$ |
| Glucose | 8.0 g $1^{-1}$ |
| Phosphoric acid (S.G. 1.75) | 0.88 g $1^{-1}$ |

This was stirred at 800 rpm at 30° C. and the pH was maintained at 7.0 by addition of ammonia. After 20 hours cultivation was made continuous by the constant addition of fresh medium containing an additional 50 mM DL-2-CPA (dilution rate 0.1 $h^{-1}$). Culture was removed at the same rate (cell dry weight 5 g $1^{-1}$) and concentrated by centrifugation to give a 10% w/v slurry of cells.

To a solution in a 450 l temperature controlled jacketted vessel which contained:
128 Kg water
23 Kg DL-2-CPA
2 Kg monosodium dihydrogen phosphate
was added 32% sodium hydroxide liquor to raise the pH to 6.0. The pH was then further raised to 7.2 by the slow addition of 20% NaOH liquor. The temperature was maintained at 30° C. by circulation of water though the vessel jacket. The vessel contents were stirred at 60 rpm.

20 Kg of cell slurry obtained as described and containing 2 Kg dry weight of cells was then charged to the vessel and a nitrogen blanket applied above the contents. The reaction was allowed to proceed under pH control at 7.2 until all D-2-CPA had been dechlorinated as judged by the addition of NaOH liquor (7.5 hours) Sulphuric acid, (78%), was then added to reduce the pH to 1.5. Clarcelflo 1 (6 Kg) (a filter aid) was added and stirred for 1 hour. The batch was then passed through a filter press and the clear filtrate was collected.

A portion of the filtrate (800 g) was added to methylisobutyl ketone (MIBK) (400 g) and stirred at room temperature for 20 minutes. The contents were then allowed to settle and were separated giving an aqueous raffinate and an MIBK extract. The raffinate was extracted a second time with MIBK. Clarcelflo 1 (10 g) was added to the MIBK extracts which were then filtered and combined. The MIBK extract was charged to a reactor and NaOH added (86.7 g of 13.47% w/w solution). After stirring for 5 minutes, settling and separation, the clear aqueous phase was adjusted to pH 7.0 by the addition of sulphuric acid to give a 28–30% w/w solution of 2-CPA, sodium salt. Examinerion by nmr (Example 2) indicated this to be L-2-CPA, sodium salt in >98% enantiomer excess (99.4% L-2-CPA : 0.6% D-2-CPA).

EXAMPLE 10

Anaerobic use of cell-free enzyme according to the fifth aspect of the invention.

*Pseudomonas putida* strain NCIB 12018 was grown and a D-2-HAA halido hydrolase enzyme was isolated from it as described in Example 1. A portion (1 ml) of the 0.15 M fraction of the cell-free extract was mixed with 5 mmoles of DL-2-CPA, sodium salt and 5 mmoles of Tris/sulphate buffer pH 9.0 in a total volume of 10 ml. This was done in duplicate. One sample was incubated in a 100 ml conical flask in a shaking water bath (60 reciprocations per min) at 30° C. The second sample was similarly incubated except that a nitrogen atmosphere was applied. The release of chloride ion from the D-2-CPA was followed in both cases and the results are shown in Table 5. From this table it can be seen that under the

TABLE 5

The release of Cl⁻ from D-2-CPA by D-2-HAA halidohydrolase incubated under air or nitrogen atmospheres.

| Time of reation (h) | concentration of chloride ion (mM) | |
|---|---|---|
| | Air | Nitrogen |
| 0 | 22.0 | 22.0 |
| 0.75 | 26.8 | 28.7 |
| 2.25 | 28.4 | 41.4 |
| 3.25 | 33.9 | 47.4 |
| 4.25 | 37.4 | 60.0 |
| 5.25 | 37.7 | 59.5 |

TABLE 5-continued

The release of Cl⁻ from D-2-CPA by D-2-HAA halidohydrolase incubated under air or nitrogen atmospheres.

| Time of reation (h) | concentration of chloride ion (mM) | |
|---|---|---|
| | Air | Nitrogen |
| 21.25 | 49.3 | 133.0 |
| 22.25 | 53.3 | 138.7 |
| 23.75 | 56.5 | 142.2 |
| 24.75 | 59.1 | 160.7 |
| 26.25 | 60.0 | 178.3 |
| 27.5 | 65.6 | 173.5 |
| 29.5 | 66.0 | 218.8 |
| 47.75 | 73.0 | 252.0 | weight of cells, was suspended in 500 mls of water containing 250 mmols DL-2-CPA, sodium salt and 50 mmols potassium phosphate buffer, pH 7.8. This was incubated at 30° C. with stirring (250 rpm) in a 1 l glass vessel. The D-2-HAA halidohydrolase activity was followed by the addition of 2 M NaOH to maintain the pH at 7.4. In a duplicate reaction, nitrogen was passed over the surface of the reaction mixture to maintain an aerobic atmosphere.

The results are given in Table 6. They show that the reaction under nitrogen continued at a higher rate and for a longer period than the reaction under air.

TABLE 6

The rate of dechlorination of D-2-CPA by D-2-HAA halidohydrolase contained in mutant bacterium AJ1-23 measured by the uptake of sodium hydroxide to maintain pH at a set point.

| Time of reaction (h) | rate of NaOH addition (mmoles h⁻¹ g cells⁻¹) | |
|---|---|---|
| | air | nitrogen |
| 2 | 6.8 | 8.7 |
| 3 | 7.2 | 8.8 |
| 4 | 6.9 | 8.2 |
| 8 | 3.0 | 6.2 |
| 12 | 1.3 | 5.0 |
| 16 | 0.8 | 4.8 |
| 20 | — | 4.2 |
| 24 | — | 2.4 |

PA/JNA/MP
9 October 1985. L105

I claim:

1. A cell-free enzyme composition which comprises a D-2-HAA-halidohydrolase which is produced by a bacterium, which cell-free enzyme composition is substantially free of any enzyme activity which is capable of metabolising a L-2-HAA or derivative thereof.

2. A biologically pure culture of a bacterium which comprises a D-2-HAA halidohydrolase and which does not contain an enzyme which is capable of metabolizing a L-2-HAA or derivative thereof.

3. A process for increasing the concentration of the L-enantiomer in a mixture of the D- and L- enantiomers of a 2-HAA which process comprises the step of treating the mixture with a D-2-HAA halidohydrolase under conditions such that at least a portion of the D- enantiomer is converted into a 2-hydroxyalkanoic acid or derivative thereof.

4. A process for the preparation of a cell-free enzyme composition according to claim 1 which comprises culturing a bacterium selected from the group consisting of strains NCIB Nos. 12018, 12158, 12160 and 12161 and mutants thereof, lysing the cells, separating the soluble protein fraction therefrom and isolating said enzyme.

5. A process for increasing the concentration of the L-enantiomer in a mixture of the D- and L- enantiomers of a 2-HAA which process comprises the step of treating the mixture with a D-2-HAA halidohydrolase under conditions such that at least a portion of the D-enantiomer is converted into a 2-hydroxyalkanoic acid wherein this step is carried out under anaerobic conditions.

6. Biologically pure cultures of bacterial strains NCIB Nos. 12018, 12158, 12159, 12160 and 12161 and mutants thereof which can be used as sources for the bacterium according to claim 2.

7. A process according to claim 3 wherein the 2-HAA is 2-bromo- or 2-chloro- propionic acid.

8. A process according to claim 3 when used to produce a 2-hydroxyalkanoic acid.

9. A process according to claim 8 wherein the 2-hydroxalkanoic acid is lactic acid.

10. A process according to claim 5 wherein the D-2-HAA halidohydrolase treatment step is conducted under nitrogen.

* * * * *